United States Patent
Cerda et al.

(10) Patent No.: US 8,697,450 B2
(45) Date of Patent: *Apr. 15, 2014

(54) MEASURING LEVELS OF A METABOLITE (71) Applicant: PerkinElmer Health Sciences, Inc., Waltham, MA (US)

(72) Inventors: Blas Cerda, Milford, MA (US); Alex Cherkasskiy, West Roxbury, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/785,655

(22) Filed: Mar. 5, 2013

(65) Prior Publication Data

US 2013/0244269 A1 Sep. 19, 2013

Related U.S. Application Data (63) Continuation of application No. 13/566,045, filed on Aug. 3, 2012, now Pat. No. 8,415,162, which is a continuation of application No. 12/843,588, filed on Jul. 26, 2010, now Pat. No. 8,257,977.

(60) Provisional application No. 61/228,444, filed on Jul. 24, 2009.

(51) Int. Cl.
  *G01N 33/92* (2006.01)
  *G01N 33/74* (2006.01)

(52) U.S. Cl.
  USPC ............ 436/71; 436/56; 436/63; 436/128; 436/131; 436/173; 436/174; 422/430

(58) Field of Classification Search
  USPC ............ 436/8, 13, 56, 63, 71, 127, 128, 131, 436/139, 140, 173, 174; 422/430; 73/1.01, 73/1.02, 1.03
  See application file for complete search history.

(56) References Cited

U.S. PATENT DOCUMENTS

| | | | |
|---|---|---|---|
| 7,985,589 B2 | 7/2011 | Garner et al. | |
| 8,227,251 B2 | 7/2012 | Ranish et al. | |
| 8,257,977 B2 * | 9/2012 | Cerda et al. | 436/71 |
| 8,415,162 B2 * | 4/2013 | Cerda et al. | 436/71 |
| 2007/0004045 A1 | 1/2007 | Xu et al. | |
| 2007/0259445 A1 | 11/2007 | Cerda | |
| 2008/0274556 A1 | 11/2008 | Cerda et al. | |
| 2011/0301063 A1 | 12/2011 | Netzel et al. | |

OTHER PUBLICATIONS

Guo et al., Clinica Chimica Acta, vol. 372, 2006, pp. 76-82.
Hall et al., Rapid Communications in Mass Spectrometry, vol. 17, 2003, pp. 2797-2803.
Watson et al., Biomedical Chromatography, vol. 5, 1991, pp. 153-160.

* cited by examiner

*Primary Examiner* — Maureen Wallenhorst
(74) *Attorney, Agent, or Firm* — Fish & Richardson P.C.

(57) ABSTRACT

Described herein are methods for determining an amount of an analyte in a test sample. The methods involve preparing a calibration curve using standard samples containing an isotopically-labeled standard in a biological matrix.

14 Claims, 6 Drawing Sheets

Testosterone, (3,4-$^{13}$C; 2,2,4,6,6,-$^{2}$H)

4-Androstene-3,17-Dione, (3,4-$^{13}$C;2,2,4,6,6,-$^{2}$H)

Dehydroepiandrosterone, (3,4-$^{13}$C;2,2,3,4,4,6,-$^{2}$H)

Progesterone, (3,4-$^{13}$C; 2,2,5,6,6,17a,21,21,21-$^{2}$H)

FIG. 4C

MEASURING LEVELS OF A METABOLITE

CROSS-REFERENCE TO RELATED APPLICATIONS

This application is a continuation of U.S. application Ser. No. 13/566,045, filed on Aug. 3, 2012, now U.S. Pat. No. 8,415,162, issued on Apr. 9, 2013, which is a continuation of U.S. application Ser. No. 12/843,588, filed on Jul. 26, 2010, now U.S. Pat. No. 8,257,977, issued on Sep. 4, 2012, which in turn claims priority to U.S. Provisional Application Ser. No. 61/228,444, filed on Jul. 24, 2009. Each of these applications is incorporated by reference in its entirety.

TECHNICAL FIELD

This document relates to methods and materials for determining an amount of an analyte in a sample using a mass spectrometry technique.

BACKGROUND

Mass spectrometry is an important analytical technique for determining the levels of many clinically relevant analytes in patient samples. Vitamin D metabolites and steroids are commonly tested examples of clinically relevant analytes for assessing the health state of individuals, from birth through adulthood. Improving the accuracy of measuring such analytes using mass spectrometry would allow for better detection of adverse health conditions.

SUMMARY

Described herein are methods for determining an amount of an analyte in a test sample. The methods involve preparing a calibration curve using standard samples containing an isotopically-labeled standard in a biological matrix.

For example, provided herein is a method for determining an amount of an analyte in a test sample. The method includes:
(a) providing a set of calibrator samples, each calibrator sample comprising a different amount of a first isotopically-labeled standard in a biological matrix,
(b) providing to each calibrator sample a selected constant amount of a second isotopically labeled standard, the first and second isotopically labeled standards having distinct isotope content;
(c) subjecting the calibrator samples comprising the first and second isotopically-labeled standards to mass spectrometry to determine signal intensities corresponding to the first and second isotopically-labeled standards;
(d) generating a calibration curve based on ratios of the determined signal intensities of the first and second isotopically-labeled standards as a function of the amount of the first isotopically-labeled standard in the calibrator samples;
(e) contacting a test sample with the selected constant amount of the second isotopically-labeled standard;
(f) subjecting the test sample comprising the second isotopically-labeled standard to mass spectrometry to determine signal intensities corresponding to the second isotopically labeled standard and the analyte, and
(g) using the calibration curve and the determined signal intensities corresponding to the second isotopically labeled standard and the analyte to determine the amount of the analyte in the test sample.

An analyte for use the methods described herein can include a secosteroid metabolite and a steroid metabolite. The secosteroid metabolite can be, for example, 25-hydroxyvitamin D3, 1-hydroxyvitamin D3, 1,25-dihydroxyvitamin D3, 25-hydroxyvitamin D2, 1α-hydroxyvitamin D2, and 24-hydroxyvitamin D2. For example, the analyte can be a vitamin D3 metabolite and the first isotopically-labeled standard can be selected from isotopically labeled 1,25-dihydroxyvitamin D3 and isotopically-labeled 25-hydroxyvitamin-D3. The first isotopically-labeled standard can be labeled with $^2$H, $^{13}$C, $^{15}$N, $^{18}$O, or a combination thereof. In some cases, the first isotopically-labeled standard is selected from labeled 1α,25-dihydroxyvitamin D3, $d_6$-labeled 25-hydroxyvitamin-D3, $d_3$-labeled 1,25-dihydroxyvitamin D3 and $d_3$-labeled 25-hydroxyvitamin-D3. For example, the first isotopically-labeled standard can be 25-hydroxyvitamin-D3(26,26,26,27,27,27-$d_6$).

In some embodiments, the analyte can be a vitamin D3 metabolite and the second isotopically-labeled standard is selected from isotopically labeled 1,25-dihydroxyvitamin D3 and isotopically-labeled 25-hydroxyvitamin-D3, such as $d_6$-labeled 1,25-dihydroxyvitamin D3, $d_6$-labeled 25-hydroxyvitamin-D3, $d_3$-labeled 1,25-dihydroxyvitamin D3 or $d_3$-labeled 25-hydroxyvitamin-D3. For example, the second isotopically-labeled standard is 25-hydroxyvitamin-D3(6,19,19-$d_3$).

The analyte can also be a vitamin D2 metabolite. In some embodiments, where the analyte is a vitamin D2 metabolite, the first isotopically-labeled standard is selected from 1,25-dihydroxyvitamin D2 and 25-hydroxyvitamin-D2. For example, the first isotopically-labeled standard can be 25-hydroxyvitamin-D2(26,26,26,27,27,27-$d_6$). In some cases, when the analyte is a vitamin D2 metabolite, the second isotopically-labeled standard is selected from 1,25-dihydroxyvitamin D2 and 25-hydroxyvitamin-D2. For example, the second isotopically-labeled standard can be 25-hydroxyvitamin-D2(6,19,19-$d_3$).

A steroid, as provided herein, can be selected from 11-deoxycortisol, 21-deoxycortisol, 17-α-hydroxyprogesterone, aldosterone, 4-androstene-3,17-dione, corticosterone, deoxycorticosterone, cortisol, dehydroepiandrosterone, dehydroepiandrosterone sulfate, estradiol, estriol, estrone, progesterone, 5-α-dihydrotestosterone, testosterone, pregnenolone, 17-α-hydroxypregnenolone, 5-α-androstane-3b, 17b-diol, 2-hydroxyestradiol, 4-hydroxyestradiol, high-density lipoprotein (HDL) cholesterol, low-density lipoprotein (LDL) cholesterol, and very low-density lipoprotein (VLDL) cholesterol, and the first and second isotopically labeled standards can be isotopically-labeled analogs of the selected analyte. For example, the analyte can be testosterone and an isotopically-labeled standard can be testosterone (3,4-$^{13}$C; 2,2,4,6,6-d5); the analyte can be 4-androstene-3,17-dione and an isotopically-labeled standard can be 4-androstene-3,17-dione (3,4-$^{13}$C; 2,2,4,6,6-$d_5$); the analyte can be dehydroepiandrosterone and an isotopically-labeled standard can be dehydroepiandrosterone (3,4-$^{13}$C; 2,2,3,4,4,6-d5); and the analyte can be progesterone and the isotopically-labeled standard can be progesterone (3,4-$^{13}$C; 2,2,5,6,6,17a,21,21,21-d9).

The methods described herein can use any mass spectrometry method, including, for example, LC-MS and LC-MS/MS. In some embodiments, the test sample is a biological sample. For example, the biological sample can be selected from the group consisting of blood (e.g., blood provided dried on a paper matrix), serum, plasma, saliva, and urine.

The first and second isotopically-labeled standards have distinct isotope content. In some embodiments, the first and second isotopically-labeled standards each comprise a different number of isotopic labels comprising the same isotope.

Further provided herein is a kit for determining an amount of an analyte in a test sample, comprising: an isotopically labeled calibrator standard, and an isotopically labeled internal standard, wherein the calibrator and internal standards have distinct isotope content.

DESCRIPTION OF DRAWINGS

FIGS. 2 (A) and (B) show calibration curves for exemplary standard compound $d^6$-25-hydroxyvitamin D2.

FIG. 4 shows detection of residual analytes present in samples after a stripping procedure was performed: (A) testosterone, (B) progesterone and (C) a vitamin D metabolite.

DETAILED DESCRIPTION

Described herein are methods for determining an amount of an analyte in a test sample. The methods involve preparing a calibration curve using standard samples containing an isotopically-labeled standard in a biological matrix.

In typical clinical laboratory procedures, external calibration curves using standard solutions of the compounds of interest are employed for the quantitation of the analytes in a test sample. These calibration curves cover the clinical ranges for the analytes of interest and are typically prepared in matrices that mimic as much as possible the biological samples used in the assay. In order to achieve the clinical ranges, the matrices (e.g. serum) used in the manufacturing of external calibrators are stripped from the endogenous analytes naturally present in them. Most commonly, serum or plasma matrices are processed using charcoal or resin columns. When the matrices travel through these columns, the charcoal or resin captures organic compounds present in the matrices. These stripping techniques are generally successful in removing a good number of small organic compounds. However, they are not effective in removing all natural analytes present in the matrix. For example, charcoal or resin stripping are not effective in removing vitamin D and related metabolites from serum and plasma matrices. As is described in the Examples herein, provided are external calibrators that are not affected by the presence of un-stripped endogenous analytes and thus provide the ability of constructing external calibration curves that range from true zero to high clinical and analytical ranges.

The role of a calibration curve is to permit accurate measurement of the level of an analyte in a sample. To generate a calibration curve, a series of calibrator samples having increasing concentrations of a calibrator, in this case an isotopically-labeled analyte derivative, for example, an isotopically-labeled vitamin D metabolite, as described herein in the Examples, are subjected to a mass spectrometry technique where one or more mass spectrometry signals of the calibrator are measured. As described herein, a linear calibration curve can be developed by determining a mass spectrometry signal corresponding to the amount of calibrator in each standard sample. For clinical testing, the standard samples are often biological samples that have been depleted of endogenous analyte. For example, standard samples for testing vitamin D in blood are blood serum samples that have been charcoal stripped. However, there is often an amount of analyte remaining, in this case vitamin D metabolites. By using the isotopically-labeled vitamin D metabolite as a calibrator, as described herein, the user can develop a linear multi-point calibration curve with a true zero point. The ability to determine a true zero point is useful for detecting and accurately measuring the level of an analyte present in a biological sample. Mass spectrometry can be used to detect and measure the signal intensities (e.g., peak height) of the analyte and, if desired, peak height ratios of the analyte and an internal standard can be used to determine amount of the analyte in each test sample by relating an analyte/internal standard signal ratio from the test sample to the calibration curve expressing a calibrator/internal standard ratio having a true zero point.

A calibration curve can be generated using a set of calibrator samples, each sample having a different amount of a first isotopically-labeled standard. To each of these samples, the same amount of a second isotopically labeled standard (i.e., an internal standard) can be added. The first and second isotopically-labeled standards can have distinct isotopic labeling. As described herein, a linear calibration curve can be developed by determining a mass spectrometry signal corresponding to the first standard and second standard in each calibrator standard sample and generating a calibration curve based on the ratios of the signal intensities of the first and second isotopically-labeled standards as a function of the amount of the first isotopically-labeled standard in the calibrator samples. When determining the amount of analyte in the test sample, the second isotopically labeled standard (i.e. internal standard) is added to the sample in the same amount as is present in the calibrator samples, and mass spectrometry can be used to detect and measure the signal intensities (e.g., peak height) of an analyte and the second isotopically-labeled standard in a test sample. Using the calibration curve and the determined signal intensities corresponding to the second isotopically-labeled standard and the analyte, the level of the analyte present in a biological sample is measured.

A series of standard calibration standard samples (e.g., 3, 4, 5, 6, 7, 8, 9, and 10 or more standard samples) containing an isotopically-labeled calibrator standard at increasing concentrations can be prepared. Several series having different calibrator concentration ranges can be used. Concentrations can be selected on the basis of the concentration range expected for a particular analyte and sample source. For example, a series of standard concentrations for vitamin D can include 5, 10, 20, 40, 75, and 150 ng/mL calibrator concentrations. Calibration curve standard samples can be prepared and analyzed using multiple replicates, for example, in duplicate or triplicate.

A calibrator is an isotopically-labeled derivative of the analyte of interest and can have a distinct mass and, thus, distinct mass to charge (m/z) ratio from that of the analyte. Any appropriate isotopic label can be used such as, for example, $^2H$, $^{13}C$, $^{15}N$, or $^{18}O$. For example, if the analyte of interest is the vitamin D metabolite 1α,25-dihydroxyvitamin D3, the calibrator can be an isotopically-labeled derivative of the metabolite such as $d_6$-1α,25-dihydroxyvitamin D3. In some cases, specific calibrators can include 25-hydroxyvitamin-D3(26,26,26,27,27,27-$d^6$) or 25-hydroxyvitamin-D2 (26,26,26,27,27,27-$d^6$). The isotopically-labeled vitamin D metabolites described herein are virtually chemically identical to their non-labeled counterparts except that their molecular mass differs by six daltons. This difference in mass allows a mass spectrometer to differentiate between the isotope-labeled vitamin D metabolites from the endogenous non-labeled metabolites present in the matrix. Likewise, if the analyte of interest is testosterone, the calibrator can be an isotopically-labeled derivative of testosterone, such as that shown in FIG. 3.

Preparation of calibrator standards and test samples can also include adding a constant, known concentration of one or more internal standards, referred to as a second isotopically labeled standard herein, to a sample to allow for quantitation of the analyte of interest. Generally an internal standard is used when performing quantitation using a mass spectrometry technique. This standard serves as a control for loss of analyte during sample preparation and instrument injection, and ion variability. An internal standard is generally added prior to sample preparation and analysis, and is added at the same level in every sample including the test sample and calibrator standards. The amount of internal standard used is above the limit of quantitation by the selected mass spectrometry technique but not so high as to suppress ionization of the analyte. Often the amount of internal standard used is targeted to be in the lower one third of the working calibration curve. An internal standard useful in the methods described herein can be isotopically labeled. One or more isotopic labels can be used, and when more than one is used, multiple of the same label (e.g. deuterium) or different labels (e.g. deuterium and $^{13}C$) can be present. Internal standards can also be added to a test sample to distinguish naturally occurring (endogenous) molecules. In some cases, test sample preparation can involve mixing a sample (e.g., a blood sample) with an extraction solution in which one or more internal standards have been added. Alternatively, the internal standards can be added to a mixture of a biological sample and an extraction solution at any step in the sample preparation that ensures the internal standards will not be removed from the mixture during the sample processing (e.g., after a liquid-liquid extraction or a solid phase extraction). In other cases, the internal standards can be added to the test sample in the absence of an extraction solution. In some cases, test sample preparation can include equilibration of the sample and one or more internal standards for a period of time (e.g., 5, 10, 15, 20, 25, 30, 60, 120, or more minutes). The equilibration temperature can be from about 10° C. to about 45° C., or any value in between (e.g., 15, 25, 30, 35, 37, 42, or 44° C.). In some cases, equilibration can be at room temperature for about 15 minutes.

An internal standard can be any compound that would be expected to behave under the sample preparation conditions in a manner similar to that of one or more of the analytes of interest. Typically an internal standard can be an isotopically-labeled derivative of the analyte of interest but could also be any appropriate analyte analog that is detectable by mass spectrometry and distinguishable from the analyte of interest and the calibrator by its mass to charge ratio. Exemplary isotopically-labeled internal standards are those derivatives that can be clearly differentiated from the isotope peaks of the analyte of interest. Any appropriate isotopic labels can be used including, for example, $^2H$, $^{13}C$, $^{15}N$, and $^{18}O$ or combination thereof. While not being bound by any theory, the physicochemical behavior of such stable isotopically-labeled derivative with respect to sample preparation and signal generation would be expected to be identical to that of the unlabeled analyte, but clearly differentiable on the mass spectrometer. In some cases, an internal standard can be deuterated 25-hydroxyvitamin $D_2$ or deuterated 25-hydroxyvitamin $D_3$. For example, $d_6$-labeled 25-hydroxyvitamin D2; $d_6$-labeled 25-hydroxyvitamin D3, $d_6$-labeled 1,25-dihydroxyvitamin D2; and $d_6$-labeled 1,25-dihydroxyvitamin D3 can be used. In some cases, an internal standard can be 25-hydroxyvitamin-D3(26,26,26,27,27,27-$d_6$) or 25-hydroxyvitamin-D2(26,26,26,27,27,27-$d_6$). These compounds are also suitable calibrator standards.

In some embodiments, an isotopically-labeled internal standard or calibrator standard can be a labeled steroid. For example, testosterone (3,4-$^{13}C$; 2,2,4,6,6-$d_5$); 4-androstene-3,17-dione (3,4-$^{13}C$;2,2,4,6,6-d5), dehydroepiandrosterone (3,4-$^{13}C$;2,2,3,4,4,6-d6); and progesterone (3,4-$^{13}C$;2,2,5,6,6,17a,21,21,21-d9).

Test samples appropriate for the methods described herein include any biological fluid, cell, tissue, or fraction thereof, containing or suspected of containing an analyte of interest. A test sample can be, for example, a specimen obtained from an individual (e.g., a mammal such as a human) or can be derived from such an individual. For example, a test sample can be a biological fluid specimen such as blood, serum, plasma, urine, lachrymal fluid, and saliva. A test sample can also be a tissue section obtained by biopsy, or cells that are placed in or adapted to tissue culture. Additional exemplary test samples include cultured fibroblasts, cultured amniotic fluid cells, chorionic villus sample, skin sample, hair sample and the like. A test sample can be further fractionated, if desired, to a fraction containing particular cell types. For example, a blood sample can be fractionated into serum or into fractions containing particular types of blood cells such as red blood cells or white blood cells (leukocytes). If desired, a test sample can be a combination of samples from an individual such as a combination of a tissue and fluid sample, and the like. Methods for obtaining test samples that preserve the activity or integrity of molecules in the sample are well known to those skilled in the art. Such methods include the use of appropriate buffers and/or inhibitors, including nuclease, protease and phosphatase inhibitors, which preserve or minimize changes in the molecules in the sample. Such inhibitors include, for example, chelators such as ethylenediamne tetraacetic acid (EDTA), ethylene glycol bis(Paminoethyl ether)N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al., Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz, Textbook of Clinical Chemistry, 3rd ed. Burtis and Ashwood, eds. W.B. Saunders, Philadelphia, (1999)).

In some cases, a test sample can be processed to eliminate or minimize the presence of substances which may interfere with the mass spectrometry technique. For example, prior to performing mass spectrometry, a test sample can be separated using standard techniques, such as by centrifugation, chromatography, binding to a matrix such as a filter paper, and extracting using extraction solution(s). A variety of techniques can be used according to the sample type. For example, solid and/or tissue test samples can be ground and extracted to free the analyte of interest from interfering components. A test sample can be centrifuged, filtered, and/or subjected to chromatographic techniques to remove interfering components (e.g., proteins, cells or tissue fragments). Hormonal steroids and their analogs and metabolites (compounds produced by biological transformation) can be sensitive to strong acids or alkaline solution and often are treated under neutral conditions for isolation. Some steroidal analytes are acidic and can be held in alkaline solution, while non-acidic impurities can be extracted with organic solvents. In some cases, reagents known to precipitate or bind the interfering components can be added to a test sample. For example, whole blood samples can be treated using conventional clotting techniques to remove red and white blood cells and platelets. Any appropriate method of polypeptide extraction or precipitation can be performed to deplete high abundance and high molecular weight polypeptides from a biological sample (e.g., plasma, urine) prior to mass spectrometric analysis. For example, acetonitrile polypeptide extraction/precipitation can be performed. In some cases, potassium hydroxide (KOH) or sodium hydroxide (NaOH) can be used for protein extraction/precipitation, optionally followed by centrifugation of the test sample. In some cases, immunochemistry-based protein-depletion techniques can be performed to remove high abundance proteins from a biological sample. For example, commercially-available kits such as the ProteoPrep® 20 (Sigma-Aldrich) plasma immunodepletion kit can be used to deplete high abundance proteins from plasma.

For use in the methods provided herein, a test sample can be in a variety of physical states. For example, a test sample can be a liquid or solid, dissolved or suspended in a liquid, in an emulsion or gel, or absorbed onto a substrate, such as a paper or polymer substrate.

The amount of analyte in a test sample can be measured according to the methods provided herein. A calibration curve can be developed by analyzing the differently labeled calibrator and internal standard using a mass spectrometry technique. Test samples can be subjected to a mass spectrometry technique to measure one or more mass spectrometry signals for the analyte of interest and an isotopically-labeled internal standard. The peak height ratios of the analyte and internal standard can be calculated and converted into measurements of the amount of the analyte in each test sample by comparing the analyte/internal standard signal ratio from the test sample to the calibration curve. The inverse ratios and other mathematical expressions also can be used so long as the amount of analyte detected in the test sample is determined.

Mass spectrometry analysis can be conducted with a single mass analyzer (MS), a "tandem in space" analyzer such as a triple quadrupole tandem mass spectrometer (MS/MS) and other MS configurations. As an example, tandem mass spectrometry can be used to distinguish and/or measure more than one isomer in a single sample with one analysis. For MS/MS, two mass analyzers are linked in series via a collision cell. The first mass analyzer (MS-1) is used to select one or more of the molecular ions of the analyte of interest (e.g., an ion of a particular mass-to-charge ratio (m/z)) or of the internal standard or of the calibrator. The selected ions are then transferred to a collision cell where they are fragmented by collisions with an inert gas. This process is called collisionally activated dissociation (CAD). Once the parent (sometimes referred to as precursor) ions have fragmented, the second mass analyzer (MS-2) is used to either, scan and detect all of the produced daughter (sometimes referred to as product) ions or to select and detect particular fragment ions.

The above-described mass spectrometry technique can also be referred to as multiple reaction monitoring ("MRM"). In MRM, a parent ion of interest is selected in MS-1, fragmented in the collision cell and a specific fragment ion resulting from the collisional activation is selected in MS-2 and finally detected. MS-1 and MS-2 are fixed to respectively select the corresponding parent and fragment ion pairs of interest for a predetermined amount of time (e.g., a few milliseconds). This specific parent ion-product ion transition can be considered as one detection channel. If additional analytes are to be detected, additional detection channels with specific mass transitions can be introduced in the experiment. Data from all selected mass transitions (channels) can be acquired sequentially to obtain the desired information.

Any tandem mass spectrometry instrument, including LC-MS and LC-MS/MS instruments can be used. Exemplary tandem mass spectrometers are available from: PerkinElmer, Waters Corporation, Thermoelectron, and Sciex. Commonly used tandem mass spectrometers are electrospray triple quadrupoles. An exemplary specific model is the ABI 4000 triple quadrupole tandem mass spectrometer (ABI-SCIEX, Toronto, Canada). Software for tuning, selecting, and optimizing ion pairs is also available, e.g., Analyst Software Ver. 1.4 (ABI-SCIEX).

An analyte to be measured according to the methods provided herein is detectable by a mass spectrometry technique. In some cases, analytes can be metabolites of the secosteroid vitamin D. Secosteroids such as vitamin D are similar in structure to steroids with the exception that two of the B-ring carbon atoms (C9 and 10) of the typical four steroid rings are not joined. For example, the analyte of interest can be 25-hydroxyvitamin D2 (also known as ergocalciferol), 25-hydroxyvitamin D3 (also known as calciferol or calcidiol), $1\alpha,25$-dihydroxyvitamin D3 (also known as calcitriol or $1\alpha,25$-dihydrocholecalciferol); $1\alpha$-hydroxyvitamin D2, $1\alpha$-hydroxyvitamin D3, or 24-hydroxyvitamin D2. In some cases, an analyte of interest can be a steroid or other metabolic intermediate. Steroids are terpenoid lipids characterized by a carbon skeleton with four fused rings, generally arranged in a 6-6-6-5 fashion. Steroids appropriate for the methods and materials provided herein can include, without limitation, 11-deoxycortisol; 21-deoxycortisol; 17-alpha-hydroxyprogesterone; aldosterone; 4-androstene-3,17-dione; corticosterone; deoxycorticosterone; cortisol; dehydroepiandrosterone; dehydroepiandrosterone sulfate; estradiol; estriol; estrone; progesterone; 5-alpha-dihydrotestosterone; testosterone; pregnenolone; 17-alpha-hydroxypregnenolone; 5-alpha-androstane-3b,17b-diol; 2-hydroxyestradiol; and 4-hydroxyestradiol. In some cases, an analyte of interest can be high-density lipoprotein (HDL) cholesterol, low-density lipoprotein (LDL) cholesterol, very low-density lipoprotein (VLDL) cholesterol, glucose, creatine, triglycerides, bilirubin, an electrolyte, or amylase.

Information collected according to the methods provided herein can be used to assess the health state of a mammal (e.g., a human patient), such as presence or absence of a disorder (e.g., vitamin D deficiency, a steroid imbalance, prenatal screening) or to evaluate the risk of developing such a disorder based on an excess or deficiency of an analyte of interest. For example, vitamin D metabolites are involved in many important biological processes. Thus, abnormal increases or decreases in their levels can alter biological functions within an organism. A deficiency in vitamin D metabolites is associated with several human diseases including rickets, osteomalacia, osteoporosis, hypocalcemia, and hyperparathyroidism. An excess of vitamin D metabolites can be associated with hypercalcemia. Levels of circulating vitamin D metabolites have been associated with the potential for developing certain types of cancer. Higher serum 25-hydroxyvitamin D3 levels have been associated with a decreased colorectal adenoma risk. See Peters et al., *Cancer Epidemiology Biomarkers & Prevention,* 13:546-552 (2004). Similarly, disruption of the hypothalamus-pituitary-adrenal axis can result in steroid imbalance and various disease states. For example, dysfunction of the adrenal glands is associated with cortisol and aldosterol deficiency. Decreased cortisol secretion from the adrenal is the major cause of congenital adrenal hyperplasia. A deficiency in the production of sex steroids such as estrogen or testosterone can result in the loss of secondary sexual characteristics. Alterations in sex steroids can be indicative of disorders including cancers, and natural processes such as onset of menopause. In some cases, the methods provided herein can be used to determine whether or not a mammal (e.g., a human individual) has a health state associated with altered levels of an analyte. In particular, levels of certain analytes can serve as biochemical indicators of a disorder, regardless of whether physiologic or behavioral symptoms of the disorder are manifest in the individual.

The methods described herein are useful for determining therapeutic efficacy of a particular treatment. When a treatment is selected and treatment starts, the individual can be monitored periodically by collecting biological samples at two or more intervals, measuring the expression level of an analyte corresponding to a given time interval pre- and post-treatment, and comparing expression levels over time. On the basis of any trends observed with respect to increasing, decreasing, or stabilizing expression levels, a clinician or other health-care professional may choose to continue treatment as is, to discontinue treatment, or to adjust the treatment plan with the goal of seeing improvement over time. In some cases, the individual can be offered additional or alternative therapeutic options. In some cases, changes in the level of a particular analyte can indicate compliance or non-compliance with a particular treatment plan. For example, lower than expected serum levels of 25-hydroxyvitamin D2 can indicate the individual's non-compliance with or poor response to a therapeutic regimen of vitamin D supplements. Therefore, the methods and materials provided herein are applicable to screening, diagnosis, prognosis, monitoring therapy and compliance, and any other application in which determining the amount of an analyte, such as a vitamin D metabolite, is useful.

Information collected according to the methods provided herein can be communicated to another person. For example, a researcher or diagnostician can communicate such information to a clinician or other medical professional. Any appropriate method can be used to communicate analyte level information to another person (e.g., a professional), and information can be communicated directly or indirectly. For example, a laboratory technician can input analyte level information into a computer-based record. In some cases, information can be communicated by making a physical alteration to medical or research records. For example, a medical professional can make a permanent notation or flag a medical record for communicating a diagnosis to other health-care professionals reviewing the record. Any type of communication can be used (e.g., mail, e-mail, telephone, and face-to-face interactions). Information also can be communicated to a professional by making that information electronically available to the professional. For example, information can be placed on a computer database such that a health-care professional can access the information. In addition, information can be communicated to a hospital, clinic, or research facility serving as an agent for the professional.

Figure 3:
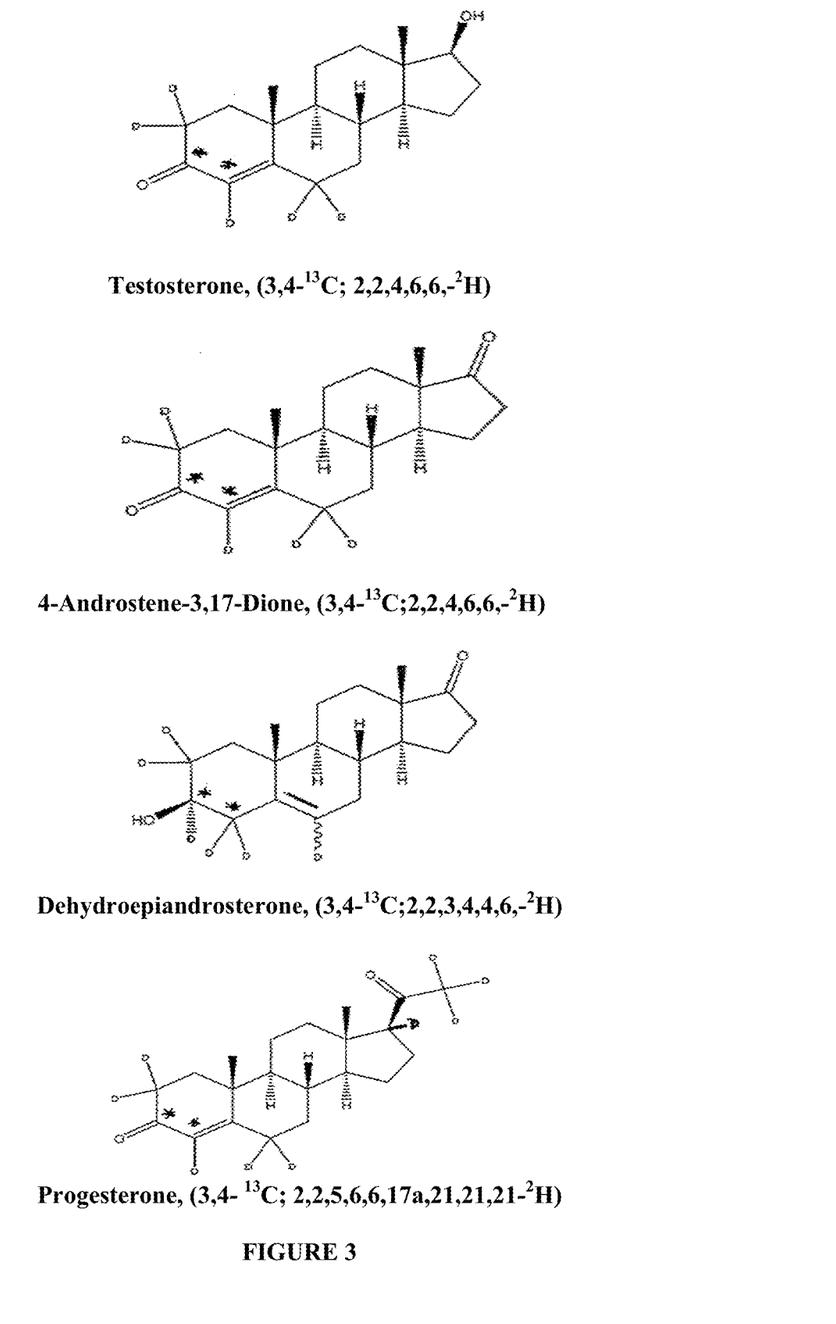
FIG. 3 shows exemplary isotopically labeled compounds.

Also provided herein are kits useful for determining the amount of an analyte in a test sample, as is described herein. Typically, a kit includes an isotopically-labeled calibrator standard and an isotopically-labeled internal standard, wherein the calibrator and internal standards can be distinguished using a mass spectrometry technique. For example, an exemplary calibrator and internal standard pair can be differently isotopically-labeled forms of the same analyte derivative, while another exemplary pair can be different analyte derivatives with the same isotopic labels. More than one type of isotopic label can be present in a calibrator and/or internal standard. In some embodiments, the isotopically-labeled standard is a biological material. In another embodiment, the kit can include an isotopically-labeled calibrator standard and an isotopically-labeled internal standard as described herein and a label that indicates that the contents are to be used for determining an amount of an analyte in a test sample. For determining the amount of a selected analyte the isotoptically-labeled internal standard and isotopically-labeled calibrator standard can be differently isotopically-labeled forms of the analyte that differ sufficiently to allow their individual detection using a mass spectrometry technique. Specific isotopically-labeled compounds useful as internal standards and calibrator standards are shown in FIG. 3.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

The invention will be further described in the following examples, which do not limit the scope of the invention described in the claims.

EXAMPLES

Example 1

This example describes use of calibration curves prepared using istopically labeled calibrator standards to accurately quantitate the amount of vitamin D analogs in quality-control samples by a mass spectrometry technique.

In order to test performance of an assay for detecting vitamin D metabolites using the isotope-labeled vitamin D standard compounds described herein, the assay detailed below was used to quantify the amount of total vitamin D (the sum of the concentrations of 25-hydroxyvitamin D2 and 25-hydroxyvitamin D3) in 5 samples provided by the vitamin D External Quality Assessment Scheme (DEQAS) (deqas.org on the World Wide Web). The DEQAS scheme regularly distributes pooled human serum samples to participating laboratories that analyze the 25-hydroxyvitamin D content of the samples and report the results back to the scheme. There are typically 400+ laboratories participating in the scheme employing 13 or more different analytical techniques. The resulting means for each analysis type and the overall "trimmed laboratory mean" is reported back to the participants.

DEQAS samples were quantified against a calibration curve of serum calibrators spiked with deuterated 25-hydroxyvitamin D2 and 25-hydroxyvitamin D3. The results described below showed good agreement between the results obtained using the labeled controls and calibrators and the results from other laboratories participating in the scheme (see Table 1).

TABLE 1

Results from DEQAS proficiency testing samples and comparison with data from other laboratories.

| | | Results from DEQAS study | | |
|---|---|---|---|---|
| DEQAS Sample | PKI measured Total D (ng/mL) | LCMS mean (ng/mL) | Diasorin Liason mean (ng/mL) | All Lab mean |
| 1 | 13.163 | 12.6 | 13.2 | 13.4 |
| 2 | 36.576 | 37.5 | 28.2 | 30.4 |
| 3 | 9.821 | 10.1 | 9.1 | 10.1 |
| 4 | 18.552 | 19.5 | 18.8 | 18.9 |
| 5 | 43.302 | 42.6 | 29.5 | 28.8 |

Figure 1A:
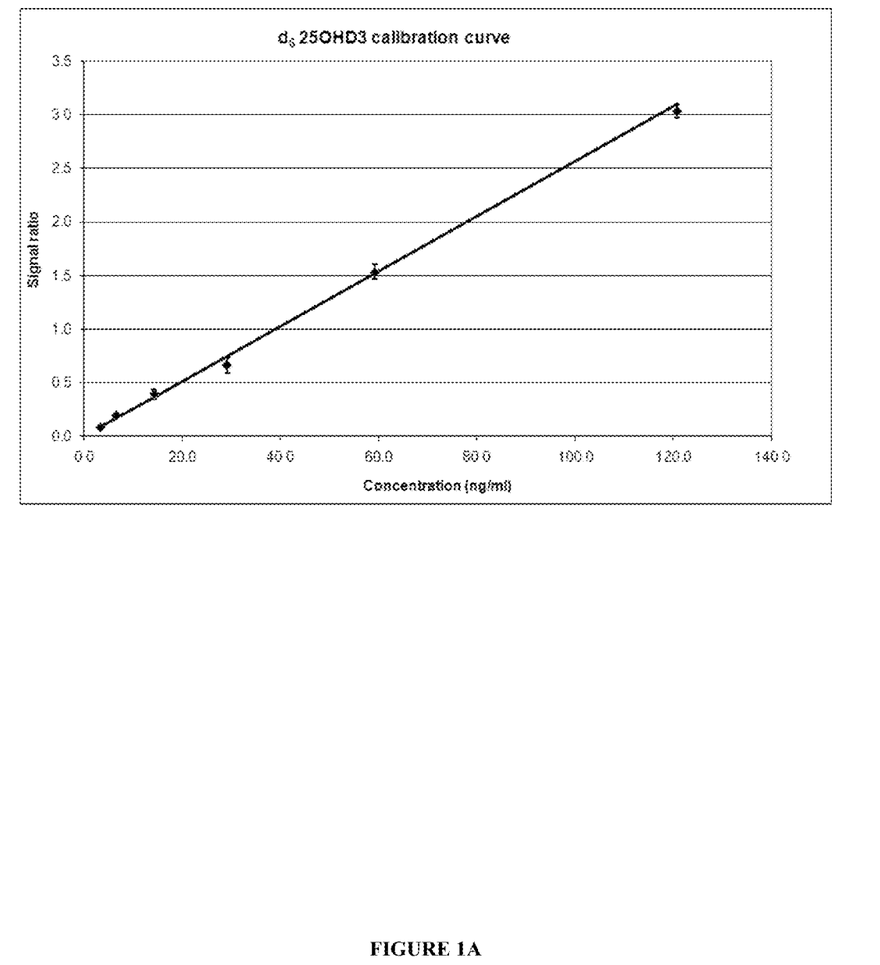
FIGS. 1(A) and (B) show calibration curves for exemplary standard compound $d^6$-25-hydroxyvitamin D3.
Figure 2A:
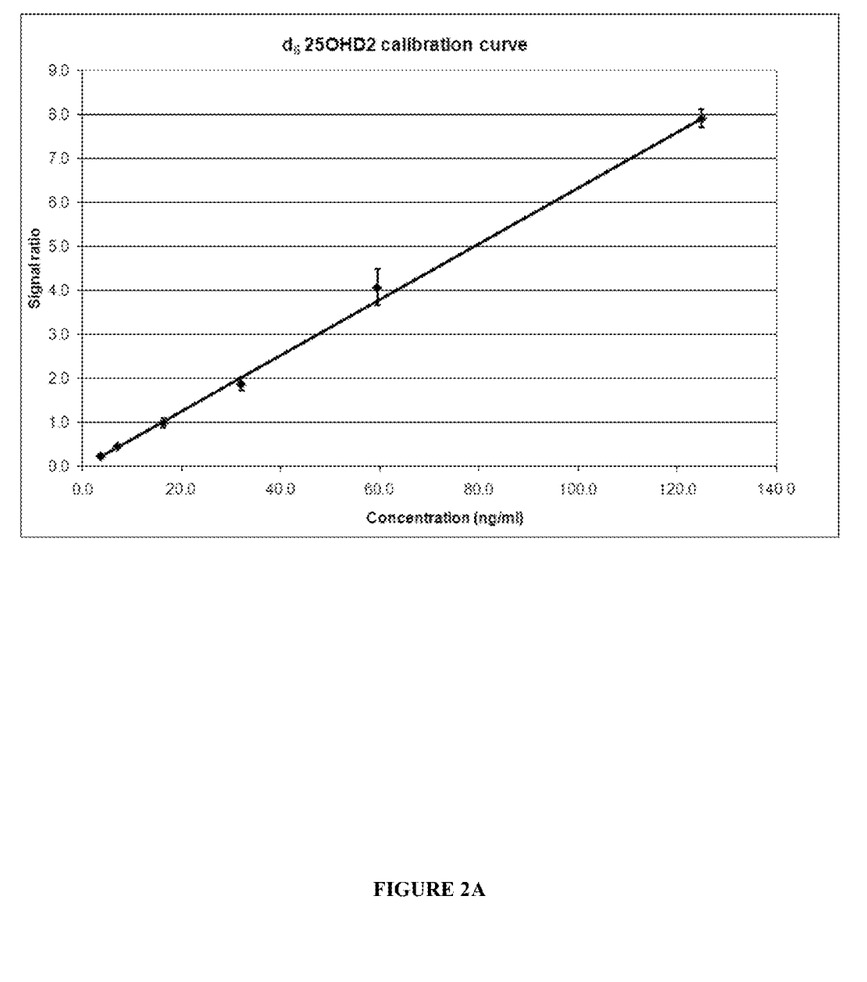

Calibration curves were constructed from the vitamin D calibrators described below and shown in Table 2. Actual spiked concentrations were determined by value assignment from a neat solution calibration curve of the labeled analytes. Analyte/internal standard ratios obtained from the DEQAS samples were compared with the kit calibration curves to determine the concentration of 25-hydroxyvitamin D2 and 25-hydroxyvitamin D3(25OHD3) in the samples. The resulting concentrations were summed to obtain the "total D" concentration for comparison with the DEQAS data. Calibration curves are shown in FIG. 1A for 25-hydroxyvitamin D3 (25OHD3) and 2A for 25-hydroxyvitamin D2(25OHD2). The data reflect average signal ratio (signal intensity of calibrator and signal intensity of internal standard) with ±1 standard deviation error bars v. concentration of calibrator.

Production of labeled calibrators was performed as follows: Heavy charcoal stripped serum was spiked with 25-hydroxyvitamin-D2(26,26,26,27,27,27-d6) and 25-hydroxyvitamin-D3(26,26,26,27,27,27-d6) to produce the following series of calibrators:

TABLE 2

Vitamin D Calibrator Levels.

| Level | d6-25OHD2 (ng/mL) | d6-25OHD3 (ng/mL) |
|---|---|---|
| 1 | 0.64 | 0.63 |
| 2 | 1.27 | 1.26 |
| 3 | 6.55 | 6.47 |
| 4 | 15.91 | 15.71 |
| 5 | 28.40 | 28.06 |
| 6 | 65.55 | 64.75 |
| 7 | 159.05 | 157.11 |
| 8 | 216.31 | 213.67 |

Calibrators were aliquoted into 3 mL amber vials (2.05 mL per vial). The calibrators were then lyophilized and frozen in order to stabilize them for subsequent use in the assay.

Lyophilized calibrators were prepared for quantitation by removing vials from −20° C. storage and thawing the serum vials to room temperature. The calibrators were then re-suspended in 2 mL of MS Grade Water, and placed on rocker for 1 hour, rotating after 30 minutes.

4-Phenyl-1,2,4-Triazoline-3,5-dione (PTAD) was prepared by weighing out about 30 mg PTAD into an amber vial, and dissolving in MS Grade Acetonitrile to a final concentration of 1.5 mg/mL.

To prepare the Daily Working Solution (DWS), specific amounts of internal standards, 25-hydroxyvitamin-D2(6,19,19-d3) and 25-hydroxyvitamin-D3(6,19,19-d3) were dissolved in acetonitrile with 0.1% formic acid to achieve a final concentration of 30 ng/mL.

The assay preparation was performed as follows (the procedure was followed to process test samples and calibrators):

1) 200 µL DWS was added to each well of a 500 µL Axygen Assay Plate.
2) 100 µL of the appropriate Serum Sample was added to each well.
3) The plate was covered with a SSP Plate Mat.
4) The plate was shaken at 25° C. at 750 rpm for 10 minutes on Wallac NCS Incubator.
5) The plate was introduced to a Hettich Rotanta 460R Centrifuge and process at 4600 rpm at 25° C. for 30 minutes.
6) The plate was carefully removed from the centrifuge and the cover was carefully removed.
7) 150 µL of the sample mixture was transfered from each well to the corresponding wells of a 350 µL Nunc Plate.
8) The sample was evaporated to dryness on Evaporex EVX-192 Plate Concentrator (Upper Temperature 45° C., Lower Temperature 80° C.). Total drying time is about 15 minutes.
9) 40 µL of PTAD solution was added to each well containing sample mixture.
10) The plate was covered with an Adhesive Microplate Cover and Shaken at 25° C. at 750 rpm for 10 minutes on Wallac NCS Incubator.
11) After incubation was complete, the derivatization reaction was quenched by adding 40 µL of 0.1% Formic Acid to each well.
12) The plate was covered with Aluminum Foil and shaken at 25° C. at 750 rpm for 10 min on Wallac NCS Incubator.
14) Processed samples were analyzed on a Waters Quattro Micro triple quadrupole.

Example 2

In order to test performance of an assay for detecting vitamin D metabolites using the isotope-labeled vitamin D calibrators described herein, the assay detailed below was used to quantify the amount of 25-hydroxyvitamin D2 and 25-hydroxyvitamin D3 in 3 serum based samples provided by National Institute of Standards and Technology (NIST, nist-.gov on the World Wide Web).

NIST standard reference material (SRM) 972 consists of multiple levels of serum based certified standards. These levels are prepared by NIST from either human serum or human/horse sera combinations. NIST SRM972 level 3 is enriched with specific levels of 25-hydroxyvitamin D2 and 25-hydroxyvitamin D3. With exception of 25-hydroxyvitamin D2 for level 1, all of the other levels are certified by NIST.

Figure 1B:
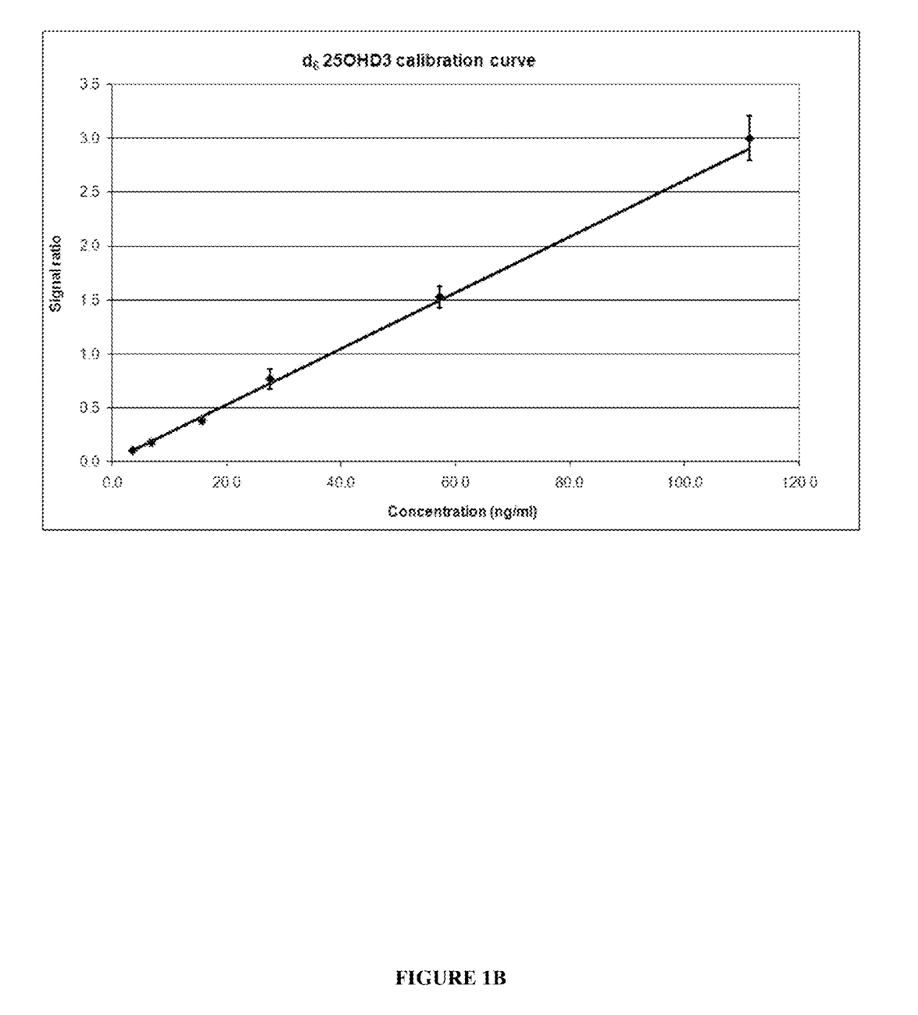
Figure 2B:
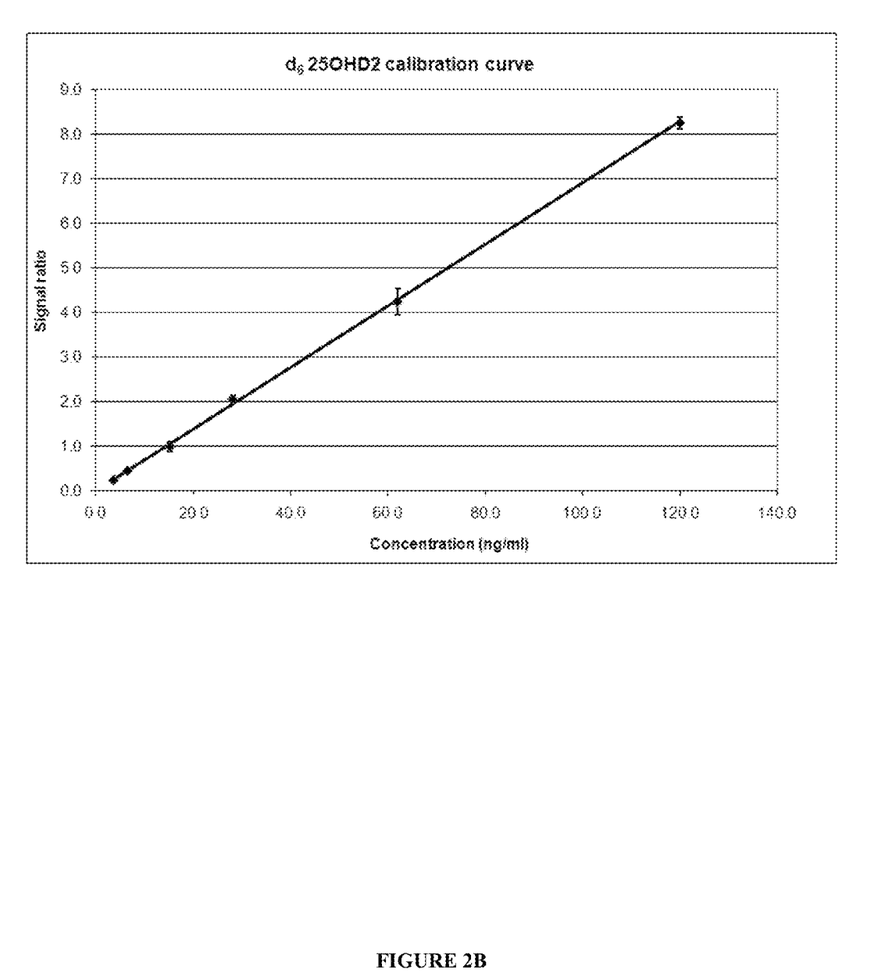

NIST SRM samples were quantified against a calibration curve of serum calibrators spiked with 25-hydroxyvitamin-D2(26,26,26,27,27,27-d6) and 25-hydroxyvitamin-D3(26,26,26,27,27,27-d6). Calibration curves were constructed from the vitamin D calibrators described below and shown in Table 3. Actual spiked concentrations were determined by value assignment from a neat solution calibration curve of the labeled analytes. Calibration curves are shown in FIGS. 1B and 2B. The data reflect average signal ratio (signal intensity of calibrator and signal intensity of internal standard) with ±1 standard deviation error bars v. concentration of calibrator.

TABLE 3

Vitamin D Calibrator Levels.

| Level | d6-25OHD2 (ng/mL) | d6-25OHD3 (ng/mL) |
|---|---|---|
| 1 | 3.71 | 3.28 |
| 2 | 7.04 | 6.51 |
| 3 | 16.32 | 14.28 |
| 4 | 32.04 | 29.09 |
| 5 | 59.52 | 59.22 |
| 6 | 124.95 | 120.80 |

Analyte/internal standard ratios obtained from the NIST samples were compared with the calibration curves to determine the concentration of 25-hydroxyvitamin D2 and 25-hydroxyvitamin D3 in the samples.

The results described below showed good agreement between the results obtained using the labeled controls and calibrators and the NIST reference and certified values (Table 4).

TABLE 4

Results from NIST SRM testing samples and comparison with reference and certified values

| NIST Sample | PKI measured (ng/mL) 25OHD2 | PKI measured (ng/mL) 25OHD3 | NIST certified or reference value (ng/ml) 25OHD2 | NIST certified or reference value (ng/ml) 25OHD3 |
|---|---|---|---|---|
| 1 | 0.50 | 24.30 | 0.6* | 23.9 |
| 2 | 1.81 | 13.22 | 1.71 | 12.3 |
| 3 | 26.64 | 19.73 | 26.4 | 18.5 |

*NIST reference value. the rest are NIST certified values.

Production of labeled calibrators was performed as described in Example 1. Serum sample preparation was performed as described in Example 1. The samples were analyzed on a Waters TQD MSMS detector employing Luna 3 µm C8(2) 100 Å 50×3.0 mm HPLC column.

Example 3

In order to test performance of an assay for detecting vitamin D metabolites using the isotope-labeled vitamin D standard calibrators as described herein, the assay detailed below was performed to quantify the amount of 25-hydroxyvitamin D2 and 25-hydroxyvitamin D3 in three artificially enriched serum samples.

Production of artificially enriched serum test samples was performed as follows: off-the-clot serum was spiked with 25-hydroxyvitamin D2(25OHD2) and 25-hydroxyvitamin D3 (25OHD3) to produce the following series of enriched samples:

TABLE 4

Vitamin D enriched samples and enrichment degree (ng/ml).

| Level | 25OHD2 (ng/mL) | 25OHD3 (ng/mL) |
|---|---|---|
| 1 | 11.9 | 0.0 |
| 2 | 23.7 | 0.0 |
| 3 | 36.6 | 0.0 |
| 4 | 49.5 | 5.1 |
| 5 | 69.3 | 10.1 |
| 6 | 89.1 | 30.0 |

Aliquots of the samples were placed into 5-mL amber vials (2.05 mL per vial) and frozen to stabilize them for subsequent use in the assay.

The enriched samples were quantified against a calibration curve of serum calibrators spiked with 25-hydroxyvitamin-D2(26,26,26,27,27,27-d6) (d6-25OHD2) and 25-hydroxyvitamin-D3(26,26,26,27,27,27-d6) (d6-25OHD3). Calibration curves were constructed from the vitamin D calibrators described below and shown in Table 5.

TABLE 5

Vitamin D Calibrator Levels.

| Level | d6-25OHD2 (ng/mL) | d6-25OHD3 (ng/mL) |
|---|---|---|
| 1 | 3.67 | 3.51 |
| 2 | 6.55 | 6.80 |
| 3 | 15.21 | 15.62 |
| 4 | 28.19 | 27.64 |
| 5 | 61.93 | 57.21 |
| 6 | 119.99 | 111.30 |

Analyte/internal standard ratios obtained from the enriched samples were compared with the kit calibration curves to determine the concentration of 25-hydroxyvitamin D2 and 25-hydroxyvitamin D3 in the samples. Examples of calibration curves for 25-hydroxyvitamin D2 and 25-hydroxyvitamin D3 are shown in FIGS. 2B and 1B, respectively.

The results described below showed good analyte recoveries (i.e. close to 100%) from the quantitation using the calibrators described herein (Table 6)

TABLE 6

Analyte recovery results (%) from enriched samples

| endogenous and enriched samples | 25OHD2 PKI measured Conc. (ng/ml) | 25OHD2 Spiked Conc. (ng/mL) | 25OHD2 % Recovery | 25OHD3 PKI measured Conc. (ng/mL) | 25OHD3 Spiked Conc. (ng/ml) | 25OHD3 % Recovery |
|---|---|---|---|---|---|---|
| endogenous | 1.5 | 0.0 | NA | 28.1 | 0.0 | NA |
| 1 | 13.5 | 11.9 | 102% | 27.1 | 0.0 | NA |
| 2 | 24.7 | 23.7 | 98% | 25.5 | 0.0 | NA |
| 3 | 40.4 | 36.6 | 106% | 32.9 | 5.1 | 94% |
| 4 | 54.7 | 49.5 | 107% | 38.9 | 10.1 | 107% |
| 5 | 71.3 | 69.3 | 101% | 61.0 | 30.0 | 110% |
| 6 | 95.2 | 89.1 | 105% | 81.2 | 49.8 | 106% |

Production of labeled calibrators was performed as described in example 2. Serum sample preparation and analysis was performed as described in Example 2.

Example 4

Figure 4A:
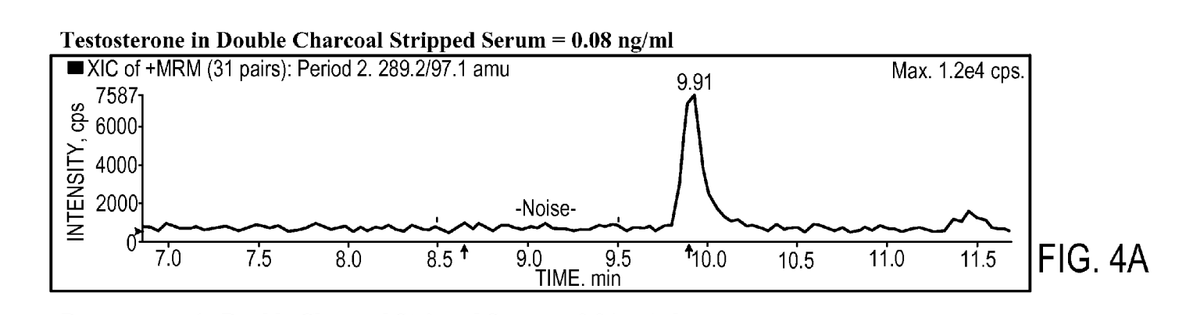
Figure 4B:
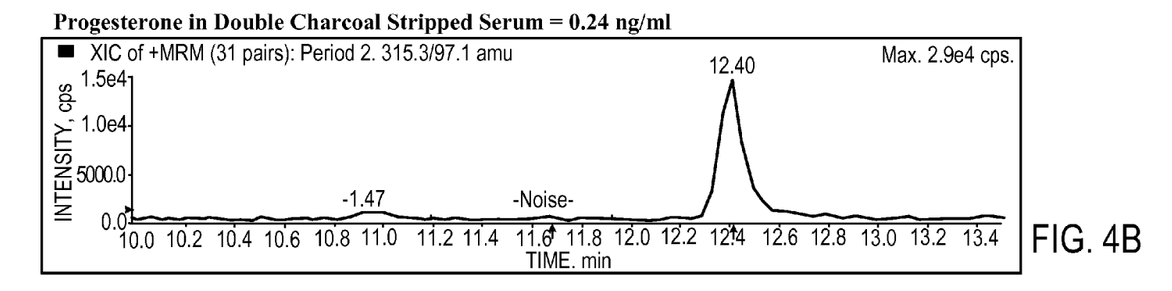
Figure 4C:
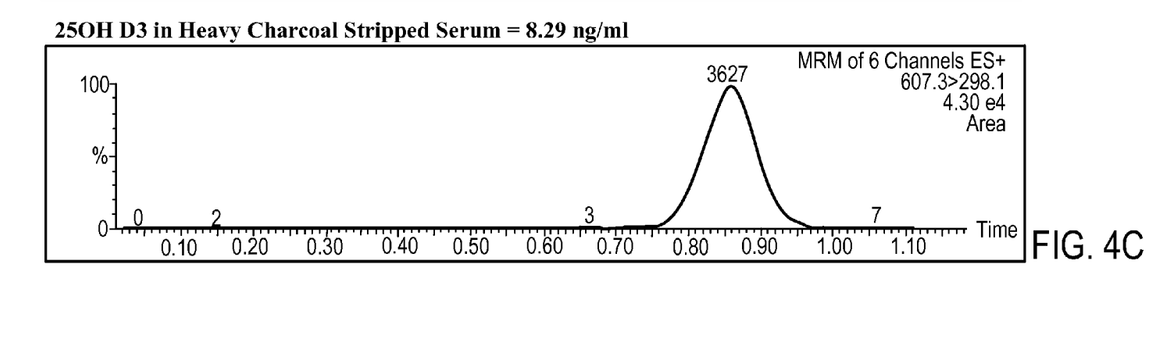

Quantitation of such analytes such as steroids and vitamin D metabolites is often performed using calibrator samples prepared using a biological matrix, such as serum. In order to quantitate clinical samples, the matrix based calibrators contain quantities of calibrators that bracket the clinically relevant concentration range. Typically, the calibrator samples are produced by first removing the endogenous analytes by either charcoal or resin stripping, followed by adding specific amounts of calibrator. However, the process of charcoal stripping is not always efficient. FIG. 4 illustrates the inefficiency phenomenon by illustrating the mass spectrum data for various samples after charcoal stripping: testosterone (A), progesterone (B), and 25-hydroxyvitamin D3 (C). In each of these samples, the respective analytes remain at appreciably higher levels than desirable for quantitation of clinical samples (lower clinical range for testosterone, progesterone and 25-hydroxyvitamin D3(25OHD3) are 0.03 ng/ml, 0.08 ng/ml and 5 ng/ml, respectively). Therefore, as described above, employing isotopically labeled standards to produce sample matrix based calibrators overcomes this inefficiency.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining an amount of a steroid metabolite in a test sample, the method comprising:
   (a) providing a set of calibrator samples, each calibrator sample comprising a different amount of a first isotopically-labeled standard,
   (b) providing to each calibrator sample a selected constant amount of a second isotopically labeled standard, the first and second isotopically labeled standards having distinct isotope content, wherein first and second isotopically-labeled standards are labeled steroid derivatives;
   (c) subjecting the calibrator samples comprising the first and second isotopically-labeled standards to mass spectrometry to determine signal intensities corresponding to the first and second isotopically-labeled standards;
   (d) generating a calibration curve based on ratios of the determined signal intensities of the first and second isotopically-labeled standards as a function of the amount of the first isotopically-labeled standard in the calibrator samples;
   (e) contacting a test sample with the selected constant amount of the second isotopically-labeled standard;
   (f) subjecting the test sample comprising the second isotopically-labeled standard to mass spectrometry to determine signal intensities corresponding to the second isotopically labeled standard and the steroid metabolite, and
   (g) using the calibration curve and the determined signal intensities corresponding to the second isotopically labeled standard and the steroid metabolite to determine the amount of the steroid metabolite in the test sample.

2. The method of claim 1, wherein the first isotopically-labeled standard is labeled with 2H, $^{13}$C, $^{15}$N, $^{18}$O, V or a combination thereof.

3. The method of claim 2, wherein the isotopically-labeled steroid derivative standard is testosterone (3,4-$^{13}$C; 2,2,4,6,6-d5).

4. The method of claim 2, wherein the isotopically-labeled steroid derivative standard is 4-androstene-3,17-dione (3,4-$^{13}$C; 2,2,4,6,6-d5).

5. The method of claim 2, wherein the isotopically-labeled steroid derivative standard is dehydroepiandrosterone (3,4-$^{13}$C; 2,2,3,4,4,6-d5).

6. The method of claim 2, wherein the isotopically-labeled steroid derivative standard is progesterone (3,4-$^{13}$C; 2,2,5,6,6,17a,21,21,21-d9).

7. The method of claim 1, wherein the second isotopically-labeled standard is labeled with deuterium.

8. The method of claim 1, wherein the steroid is selected from the group consisting of: 11-deoxycortisol, 21-deoxycortisol, 17-α-hydroxyprogesterone, aldosterone, 4-androstene-3,17-dione, corticosterone, deoxycorticosterone, cortisol, dehydroepiandrosterone, dehydroepiandrosterone sulfate, estradiol, estriol, estrone, progesterone, 5-α-dihydrotestosterone, testosterone, pregnenolone, 17-α-hydroxypregnenolone, 5-α-androstane-3b,17b-diol, 2-hydroxyestradiol, 4-hydroxyestradiol, high-density lipoprotein (HDL) cholesterol, low-density lipoprotein (LDL) cholesterol, and very low-density lipoprotein (VLDL) cholesterol, and the first and second isotopically labeled standards are isotopically-labeled derivatives of the selected steroid.

9. The method of claim 1, wherein the mass spectrometry comprises a technique selected from LC-MS and LC-MS/MS.

10. The method of claim 1, wherein the test sample is a biological sample.

11. The method of claim 10, wherein the biological sample is selected from the group consisting of blood, serum, plasma, saliva, and urine.

12. The method of claim 11, wherein the blood is provided dried on a paper matrix.

13. The method of claim 1, wherein first and second isotopically-labeled standards each comprise a different number of isotopic labels comprising the same isotope.

14. A kit for determining an amount of a steroid metabolite in a test sample, comprising:
   an isotopically labeled steroid derivative calibrator standard, and
   an isotopically labeled steroid derivative internal standard, wherein the calibrator and internal standards have distinct isotope content.

* * * * *

UNITED STATES PATENT AND TRADEMARK OFFICE
CERTIFICATE OF CORRECTION

PATENT NO. : 8,697,450 B2  Page 1 of 1
APPLICATION NO. : 13/785655
DATED : April 15, 2014
INVENTOR(S) : Blas Cerda et al.

It is certified that error appears in the above-identified patent and that said Letters Patent is hereby corrected as shown below:

In the Claims

Column 15, Claim 2, Line 49: delete "2H" and insert --$^{2}$H--.

Signed and Sealed this
Twenty-ninth Day of July, 2014

Michelle K. Lee
*Deputy Director of the United States Patent and Trademark Office*